(12) United States Patent
Kuhr et al.

(10) Patent No.: US 6,419,661 B1
(45) Date of Patent: Jul. 16, 2002

(54) DEVICE FOR WITHDRAWING BLOOD FOR DIAGNOSTIC APPLICATIONS

(75) Inventors: Hans Jürgen Kuhr, Mannheim; Richard Forster, Pfreimd, both of (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/518,799

(22) Filed: Mar. 3, 2000

(30) Foreign Application Priority Data

Mar. 5, 1999 (DE) .......................................... 199 09 602

(51) Int. Cl.$^7$ ............................................... A61M 5/00
(52) U.S. Cl. ..................... 604/207; 604/22; 604/46; 604/47; 604/167; 606/181; 606/182
(58) Field of Search .................... 604/207, 22, 46, 604/47, 167; 606/181, 182

(56) References Cited

U.S. PATENT DOCUMENTS

| | | | |
|---|---|---|---|
| 4,203,446 A | * 5/1980 | Hofert | 128/329 |
| 4,442,836 A | 4/1984 | Meinecke et al. | 128/314 |
| 4,469,110 A | 9/1984 | Slama | 128/770 |
| 4,535,769 A | 8/1985 | Burns | 128/314 |
| 4,653,513 A | 3/1987 | Dombrowski | 128/765 |
| 4,895,147 A | 1/1990 | Bodicky et al. | 606/182 |
| 4,924,879 A | * 5/1990 | O'Brien | 604/22 |
| 5,196,025 A | * 3/1993 | Ranalletta | 606/182 |
| 5,304,193 A | * 4/1994 | Zhadanov | 606/182 |
| 5,318,584 A | * 6/1994 | Lange | 606/182 |
| 5,554,166 A | 9/1996 | Lange et al. | 606/182 |

* cited by examiner

*Primary Examiner*—Ira S. Lazarus
*Assistant Examiner*—Tu C. Nguyen
(74) *Attorney, Agent, or Firm*—Richard T. Knauer; Roche Diagnostics Corporation

(57) ABSTRACT

Device for withdrawing Blood for Diagnostic Purposes. A lancet holder (8) for holding a lancet (7) and a lancet drive (12) having a loadable elastic drive spring (15) are provided within an elongated housing (2). The relaxing motion of the drive spring (15) is converted into a puncturing motion, after release of a locking device, to move the lancet (7), held by the lancet holder (8), at high speed in the puncturing direction until its tip exists out of an exit opening (5) of the housing (2).

Figure 1:
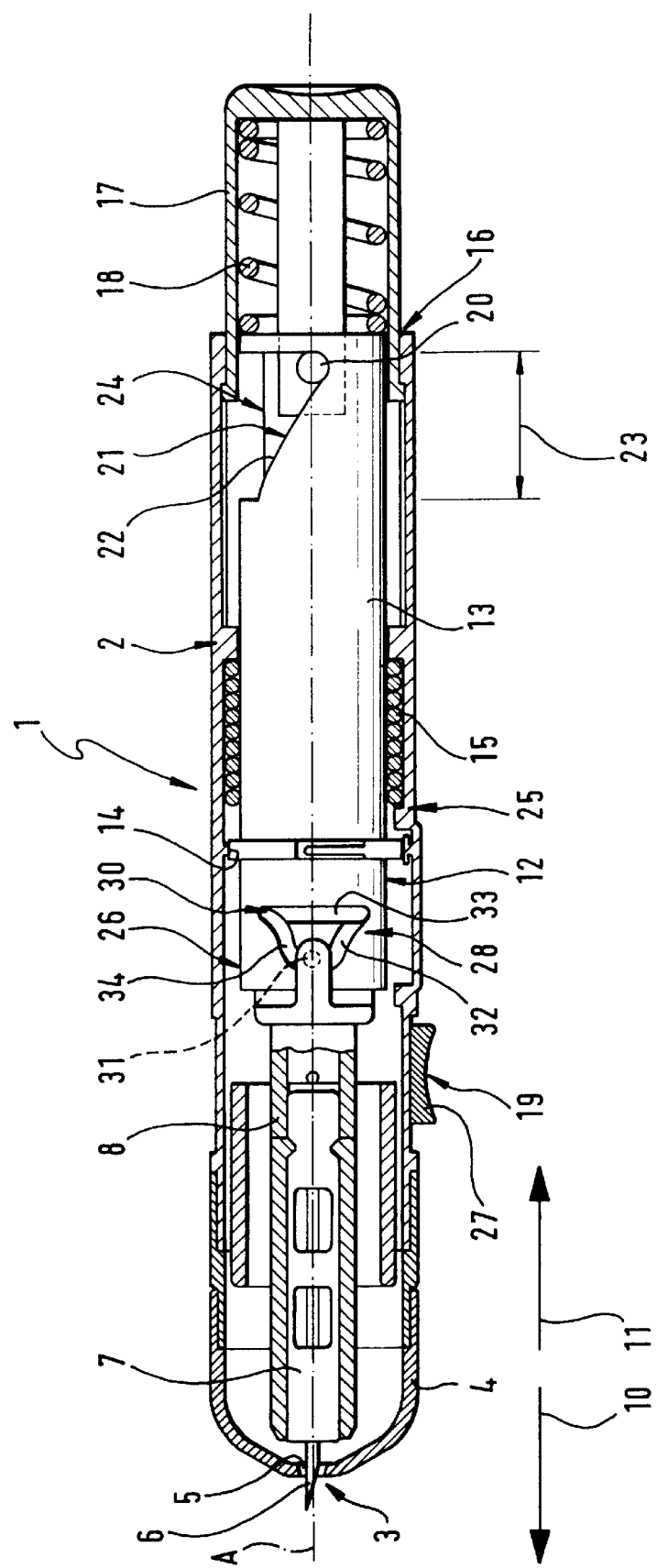

An improved handling and simultaneous minimization of pain is achieved by providing a two-sided rotary/translatory transmission (25) in the housing (2), wherein a) the input side (24) of the rotary/translatory transmission (25) transforms the motion of a loading button (17), protruding out of the rear end (16) of the housing. (2), along a linear loading path (23) into a rotational motion of a lancet drive rotor (13) which rotates about a rotational axis extending parallel to the axis of the device (A) to load the lancet drive rotor (13) by tensioning the drive spring (15);

b) when the lancet drive is triggered, the output side (26) of the rotary/translatory transmission (25) converts a rotational motion of the lancet drive rotor, driven by the drive spring, into the puncturing motion in the direction along the main axis.

14 Claims, 4 Drawing Sheets

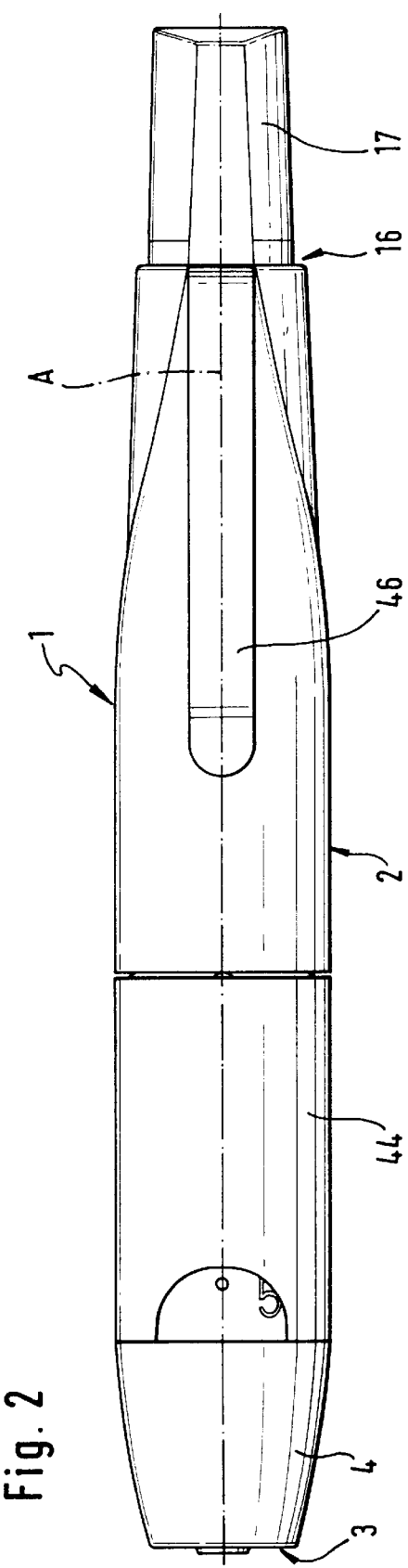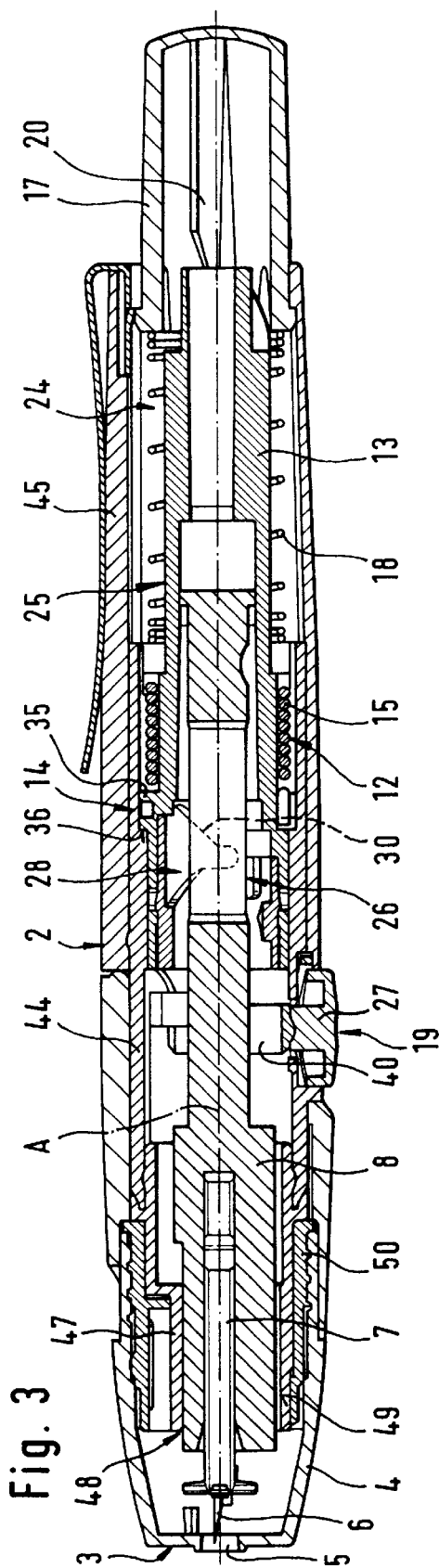

DEVICE FOR WITHDRAWING BLOOD FOR DIAGNOSTIC APPLICATIONS

The invention concerns a blood lancet device for withdrawing blood for diagnostic purposes.

Lancets are used in diagnostic applications to withdraw a small amount of blood by pricking a part of the body (usually the finger or the ear-lobe). In the past, the puncturing procedure had been carried out by trained, specially educated personal either manually or using a simple apparatus. This method to obtain a blood sample is acceptable when blood investigations must only be carried out occasionally, since in this case the pain associated with the puncturing does not play a decisive role.

The requirements for blood withdrawal are substantially more stringent when regular monitoring of certain analytic values in the blood of a patient is necessary. This is particularly the case for diabetics whose blood sugar levels must be monitored frequently and regularly in order to keep these levels (which depend on food ingestion, physical activity and other factors) within certain limiting values through the administration of insulin injections. Such an intensive blood sugar therapy is of extreme importance to the health of the patient and requires at least four blood withdrawals per day. For example, the publication "The Effect of Intensive Treatment of Diabetes on the Development and Progressing of Long-term Complications in Insulin-dependent Diabetes Mellitus", of the Diabetes Control and Complications Trial Research Group, New England Journal of Medicine, 1993, 977 to 986 reports that intensive therapy, involving at least four blood samples per day, can reduce the probability of retinopathy (which eventually leads to blinding of the patient) by 76%. This is also the case for other serious long term damage associated with diabetes mellitus.

Long-term intensive blood sugar therapy is only feasable by so-called "home-monitoring" carried out by the patient himself or by family members without the use of trained medical personal. The willingness and capability of the patient to obtain a blood sample by means of a lancet at least four times daily depends decisively on the properties of the blood withdrawal device. It must be so designed that the pain associated with generation of the wound necessary for blood withdrawal is as low as possible. The device must be as simple to operate as possible, since a large share of the patients are, due to their illness or advanced age, not capable of carrying out difficult manual operations in a precise fashion. In addition, low weight and a practical shape are important in order that the device can be easily carried along with the patient. In addition, the design should be as simple as possible, it should be durable, and inexpensive.

Blood withdrawal devices and associated lancets have been proposed having various structural configurations to satisfy these requirements. They are described, by way of example, in the following US patents:

April 1984 U.S. Pat. No. 4,442,836 Meinecke
August 1985 U.S. Pat. No. 4,535,769 Burns
September 1984 U.S. Pat. No. 4,469,110 Slama
March 1987 U.S. Pat. No. 4,653,513 Dombrowski
January 1990 U.S. Pat. No. 4,895,147 Bodicky
May 1990 U.S. Pat. No. 4,924,879 O'Brien
June 1994 U.S. Pat. No. 5,318,584 Lange
September 1996 U.S. Pat. No. 5,554,166 Lange.

Although these known designs provide substantial improvements in blood withdrawal for diagnostic purposes, they cannot completely satisfy all of the previously mentioned requirements. In particular, those devices which produce the wound with very low pain levels have disadvantages with regard to handling and/or shape and size of the device. Conversely, small and easily operated devices are associated with insufficiently low pain levels.

It is an object of the invention to create an improved blood withdrawal device which better satisfies the above mentioned requirements.

The purpose is achieved by a device for withdrawing blood for diagnostic applications, comprising an elongated housing on the front end of which an exit opening is provided for the tip of a lancet, a lancet holder which holds the lancet and which can be displaced within the housing in the direction of its main axis along a predetermined puncture path, a lancet guide for guiding the lancet holder along the predetermined puncture path and a lancet drive having a resilient drive spring which can be locked in a loaded state using a locking device and which converts the relaxing motion of the drive spring into a puncture motion after the locking device is released, wherein the lancet, held by the lancet holder, is moved with high velocity along the predetermined puncture path in the puncture direction until its tip exits out of the exit opening to produce a wound in a part of the body proximate the exit opening, and wherein a two-sided rotary/translatory transmission is provided in the housing, the entrance side of the rotary/translatory transmission converting the motion of a loading button, projecting out of the rear end of the housing and movable along a linear loading path into a rotational motion of a lancet drive rotor which rotates about a rotational axis running parallel to the axis of the device to load the lancet drive rotor by tensioning the drive spring, the exit side of the rotary disk converting, after release of the lancet drive, a rotational motion of the lancet drive rotor driven by the drive spring into the puncturing motion in the direction of the main axis.

The invention is also directed to a blood withdrawal kit comprising the following mutually adapted system components: a blood withdrawal device in accordance with the invention and lancets adapted to be held in the lancet holder of the device. Such blood withdrawal kits (which also can be referred to as blood withdrawal equipment) are initially sold in the form of a packaged unit containing both system components. Since the lancets can normally only be used once, they are also provided in separate packages for use by patients already having blood withdrawal devices.

The term "transmission" is to be understood in its general sense i.e. in terms of a kinematic device for coupling and converting motion. In the present case, the double sided rotary/translatory transmission transforms a translation motion of the loading button into a rotational motion of the lancet drive rotor and a rotational motion of the lancet drive rotor into a translational motion of the lancet holder and lancet. These transmission functions can in principle be realized by means of conventional mechanical engineering elements.

The invention has the following advantages:

It allows a very slim housing shape similar to a ballpoint pen (so-called pencil shape). The device is inconspicuous and easily carried by the user.

The device can be loaded and triggered using one hand only.

The device is operated in a simple and logical manner.

Very little pain is produced by the wound. This is partially due to the associated very low vibration level.

Despite these substantial improvements in function, the structure is simple and inexpensive.

Embodiments of the invention should take into consideration the fact that a low-pain puncture requires a very rapid and precise puncturing motion. To this end the drive spring should have a high spring constant. On the other hand, the loading button should be sufficiently easy to operate such that older and physically handicapped people can load the blood withdrawal device.

These problems are solved in a particularly effective fashion and the above mentioned advantages are realized to a particularly good degree using preferred embodiments having the features described hereafter and in the dependent claims. These features can be used in the blood withdrawal device of the invention either individually or in combination.

In accordance with a preferred embodiment, the lancet drive rotor comprises a slide surface running along a helical path and the loading button comprises a loading cam which slides via a contact surface on the slide surface of the helical path to convert a linear motion of the loading button into a rotational motion of the lancet drive rotor. The helical path is preferentially formed on a loading sleeve constituting a part of the drive rotor. The forward end of the loading sleeve facing the exit opening surrounds the lancet holder.

In accordance with an additional preferred embodiment of simple construction and having low vibration, a guiding cam is provided in proximity to the front end of the loading sleeve. It controls, in cooperation with a guide pin provided on the lancet holder, the puncturing motion and preferentially also the return motion of the lancet holder and the lancet contained therein. Control of the puncturing and return motions through cooperation between a guide pin and a guide cam is disclosed in the above mentioned US patents 5,318,584 and 5,554,106.

The invention is described more closely below in an embodiment shown in the figures.

Figure 4:
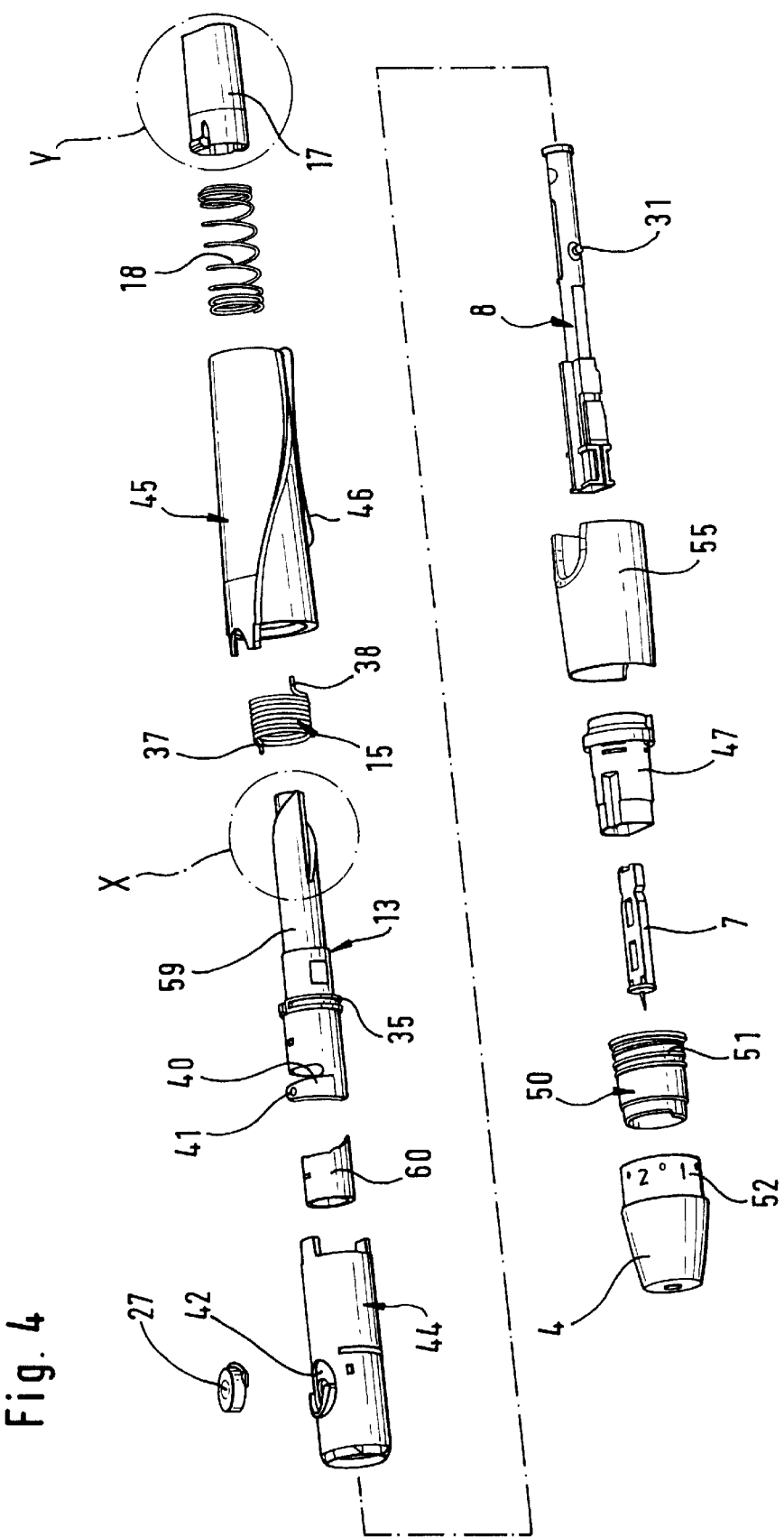
Figure 5:
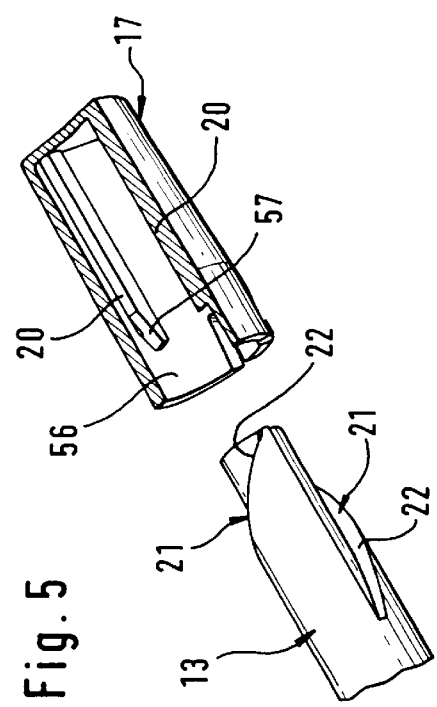
Figure 6:
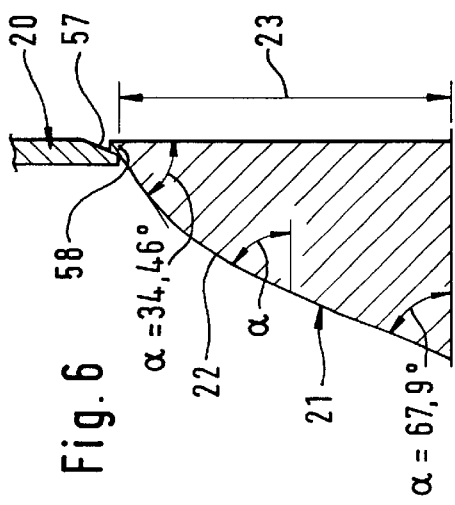
Figure 7:
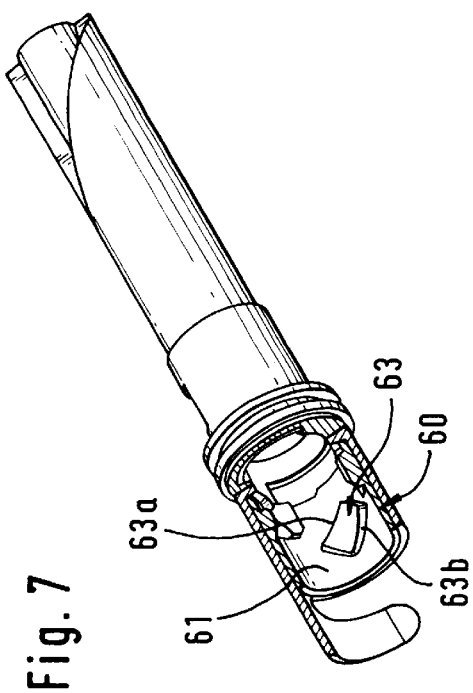
Figure 8:
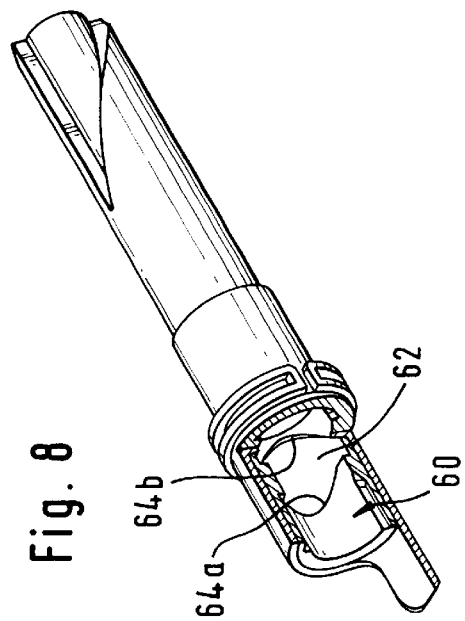

FIG. 1 shows a schematic representation of a blood withdrawal device in section, FIG. 2 shows a side view of a blood withdrawal device, FIG. 3 shows a cross-section of the blood withdrawal device of FIG. 2 having a lancet inserted in the lancet holder, FIG. 4 shows an exploded view of a blood withdrawal device showing the important functional components thereof in accordance with the present invention, FIG. 5 shows a detailed representation of the rearward end of the lancet drive rotor shown in FIG. 4 and of the loading button shown in FIG. 4, wherein the latter is cut open, FIG. 6 shows an unfolded planar representation of the loading sleeve helical path shown in FIGS. 2 and 3, FIG. 7 shows a first cut open view of a loading sleeve shown in FIG. 4 with an inserted cam guide bushing, and FIG. 8 shows a second cut open view of the loading sleeve and cam bushing of FIG. 7.

The blood withdrawal device 1 schematically shown in FIG. 1 comprises an elongated housing 2 extending along the main axis of the device A. A removable cap 4 is disposed at the front end 3 of the housing and has an exit opening 5 for the tip 6 of a lancet 7.

The lancet 7 is held by a lancet holder 8 in such a fashion that the position of the tip 6 relative to the holder 8 is reproducibly the same when a new lancet 7 is inserted into the holder for subsequent blood withdrawal. U.S. Pat. No. 5,318,584 discloses advantageous mechanisms for achieving this goal which can also be used in the present invention.

The front end 3 of the housing 2 is pressed against a body part in which a wound is to be produced in order to obtain a drop of blood. The lancet holder 8 then makes a puncturing motion to propel the lancet 7, held in the lancet holder 8, at high velocity along a predetermined puncturing path preferentially extending along the main axis A in the puncture direction symbolized by the arrow 10 until its tip 6 exits from the opening 5 and penetrates into the body part. The lancet 7 is then returned to its initial position in the return direction indicated by arrow 11.

The puncturing and return motion of the lancet holder 8 (and thereby the lancet 7) is driven by a lancet drive (designated in, its entirety with 12) whose central element is a lancet drive rotor 13 borne by a rotation bearing 14 for rotation about the main axis A in a fixed axial position in the housing 2. The lancet drive rotor 13 is connected to a drive spring 15, configured as a torsion spring surrounding the drive rotor 14. One end of the drive spring 15 is attached to the lancet drive rotor 13 and the other end to the housing 2.

The drive spring 15 is loaded by rotating the lancet drive rotor 13 in opposition to its spring force. In the embodiment shown, a leftward rotation of the rotor 13 (as viewed from the rear end 16 of the housing) is required. This loading motion is effected by moving a loading button 17 along the main axis A towards the front end 3. The loading button 17 projects out of the rear end 16 of the housing 2 and is loaded by a restoring spring 18 in opposition to this motion. A loading cam 20 is fixed to the loading button 17 and travels along slide surface 22 which runs along a helical path 21 fashioned on the drive rotor 13. The loading button 17 and the associated loading cam 20 are guided to be axially displaceable but to prevent rotation. The shape of the helical path 21 thereby leads to a transformation of the motion of the loading button 17, along a linear loading path symbolized by arrow 23, into rotation of the lancet drive rotor about a rotational axis extending parallel to the main axis. Thus, the lancet drive rotor 13 is loaded by tensioning the drive spring 15. After loading, the lancet drive rotor is locked in the loaded position using a locking device 19 (not shown in detail in FIG. 1). The loading button 17 with the cam 20 and the drive rotor 13 with the helical path 21 guiding surface 22 constitute the input side, designated in its entirety with 24, of a two-sided rotary/translatory transmission 25.

The output side 26 of the two-sided rotary/translatory transmission 25 is configured to convert, after the lancet drive is triggered via a trigger button 27 (the function of which is not shown in FIG. 1),the rotational motion of the lancet drive rotor 13, driven by the drive spring 15, into the puncturing motion 10 along the main axis A. This is done using a cam mechanism 28 comprising a cam guide 30 and a guide pin 31 fitting into the cam guide . The guide pin 31 is fixed to the lancet holder 8 and the lancet holder 8 is borne such that it may be displaced axially, but not rotated. The cam guide 30 is fashioned by a recess 32 in the lancet drive rotor 13. It is shaped such that during the loading motion the guide pin 31 travels through a first section 33 of the cam guide 30 which, in the embodiment shown, is substantially straight and runs transverse to the main axis A. During the puncturing and return motion, the guide pin 31 passes through a second section 34 of the cam guide 30 which initially extends towards the front end 3 and then towards the rear end 16 to thereby effect a defined puncturing and return motion of the holder 8. Further details concerning this type of structure can be taken from the above mentioned U.S. Pat. No. 5,318,584 showing a design in which the cam guide is part of the lancet holder and the guide pin rotates. In the present invention, these functions are preferentially reversed: the guide pin 31 is firmly attached to the lancet holder 8 for axial motion, whereas the cam guide 30 rotates with the lancet drive rotor 13.

FIGS. 2 through 8 provide differing representations of a particularly preferred practical embodiment of a blood withdrawal device in accordance with the invention. The figures are drawn to scale, i.e. the relative proportions of the components in each of the figures correspond to the actual relationships. The components described on the basis of FIG. 1 are designated with the same reference symbols in FIGS. 2 through 8 and will not be described again.

As shown in FIGS. 3 and 4, the rotation bearing 14 is advantageously formed by a bearing ring 35 fashioned on and protruding past the peripheral surface of the lancet drive rotor 13 and cooperating with an associated shoulder 36 of the housing 2. The bearing ring 35 has an interruption into which the first leg 37 of the drive spring 15 engages. The second leg 38 is fixed to the housing 2.

FIGS. 2 through 4 show the preferred structure of the housing 2. The lancet drive 12 is surrounded by two axially joinable housing portions: a front housing portion 44 and a rear housing portion 45. The blood withdrawal device 1 can e.g. be secured within a suit jacket pocket using a clip 46 disposed on the rear housing portion 45. A lower insert member 47 is inserted into the front housing portion 44 and has a central axial opening 48 whose inner shape corresponds to the outer shape of the lancet holder 8. The walls of the axial opening 48 provide a precise guide 49 for the puncturing and return motion of the lancet holder 8.

The lower end of the insert member 47 is surrounded by an adjustment ring 50 having a thread provided on its outer side 51 onto which the cap 4 is screwed. The longitudinal position of the cap 4 relative to the lancet holder 8 can be changed to adjust the puncturing depth through rotation of the cap 4 relative to the adjustment ring 50. The adjustment position is indicated by a scale 52 on the cap 4.

In the embodiment shown, the locking device 19 comprises a resilient tab 40 on the lancet drive rotor 13. A short locking pin 41 extends radially outwardly past the resilient tab 40 to engage into an associated opening 42 of the housing member 44 and lock the lancet drive in the loaded state of the spring 15. For triggering, the trigger button 27 is pressed at its lower triggering end into the opening 42 to free the locking pin 41. The trigger button 27 is preferentially transparent so that the locking pin 41, and optionally, portions of the resilient tab 40 can be viewed through the trigger button 27 in the loaded state of the locking pin 41. These components are preferentially given a contrasting color (e.g. yellow or red) to provide simple recognition of the loaded state of the blood withdrawal device 1.

The lower housing portion 44 and the cap 4 are partially surrounded by an ejection sleeve 55. The ejection sleeve 55 can expel the lancet 7 from the holder 8 after the cap 4 and the adjustment ring 50 are removed from the lower end of the housing 2.

FIGS. 5 and 6 illustrate details of a particularly preferred configuration of the input side 24 of the two-sided rotary/translatory transmission.

As can be seen in FIG. 5, two helical paths 21 with parallel running slide surfaces 22 are fashioned on the rear end of the lancet drive rotor 13 and cooperate with associated loading cams 20 disposed on the inner wall 56 of the loading button 17. During loading, the loading cams 20 each slide along the slide surfaces 22 of the helical path 21 with their diagonally tilted contact surfaces 57.

FIG. 6 best shows a particularly advantageous configuration in which the slope of the helical path 21 (i.e. the angle α between the guiding surface and a straight line perpendicular to the main axis and passing through the guiding surface at the respective point) varies along the length of the loading path 23. The angle α preferentially increases, at least in sections, along the length of the helical path (corresponding to the length of the loading path 23 of cam 20) in the direction towards the front end 3 of the housing 2. In a particularly preferred embodiment, this increase is continuous. In the exemplary embodiment shown in FIG. 6, the angle α is approximately 68° at the front end of the helical path and approximately 34.5° at the rear end. The slope should change in such a fashion that, during loading, the force which has to be exercised on the loading button 17 is substantially constant at least in sections along the loading path 23. Since the restoring force of the drive spring 15 increases during the loading process, the transmission ratio of the input side 24 of the rotary/translatory transmission should be relatively large at the beginning of the loading process and should decrease continuously along the loading path 23. This is achieved by increasing the slope angle α.

The contact surface 57 of loading cam 20 is preferentially slanted in such a fashion as to assure area contact with the helical path at least along a portion of that half of the length of the helical path which is closer to the front end of the housing. In the embodiment shown in the figures, the slant of the contact surface 57 is equal to the slope of the guiding surface 22 in the front section (lower section in FIG. 6) thereof. This facilitates a particularly smooth sliding at low wear in that region of the loading process which has the highest opposing forces of the spring 15.

The helical path 21 has a ramped starting section 58 fashioned at its end facing the rear 16 of the housing 2 to reduce stress associated with the initial contact of a loading cam 20, configured in the above described fashion, on the slide surface 22 of the helical path 21. The starting section 58 has a slope which corresponds to that of the slide surface. Although the contact surface of the loading cam 20 at the lower end of the ramp-shaped starting section 58 briefly contacts only along a narrow line, excessive wear does not occur in this region due to the low spring force. Rather this preferred embodiment is extremely easy to operate.

The choice of material used for the lancet drive rotor 13 (at least the slide surface 22 thereof) and for the loading cam 20 (at least the contact surfaces 57 thereof) is important for easy operation. The former preferentially comprises a plastic based on polyacetal material, in particular, based on a polyoxymethylene (POM). A styrene-acrylnitril-copolymer (SAN) based plastic is particularly well suited for the latter.

As shown in FIGS. 3, 4, 7 and 8, the lancet drive rotor 13 consists essentially of two parts: a loading sleeve 59 and a cam bushing 60. The cam bushing 60 can be inserted into the loading sleeve 59 from the front. The front end of the loading sleeve 59, with the cam bushing 60 inserted therein, surrounds the rear end of the lancet holder 8 in the region in which the lancet holder 8 has two diametrically opposed guide pins 31. The loading sleeve 59 and the cam bushing 60 inserted therein form two recesses in the lancet drive rotor 13 whose bordering edges together define a cam guide. The recesses 61 and 62 are fashioned in such a manner that during each phase of the rotational motion one of the recesses 61 guides a guide pin rearwardly and the other recess 62 guides a guide pin forwardly.

In the embodiment shown, the rear edge 63a of the raised area 63 (see in FIG. 7) limits the motion of a control pin 31 during the return phase in a forward direction. Thus, motion of the lancet holder 8 in the forward direction is limited by the rear edge 63a of the raised area 63. The forwardly facing edge 63b of the raised area 63 correspondingly limits motion of the lancet holder 8 towards the rear during the puncturing and return phase.

During the puncturing and return phase the freedom of motion of the lancet holder 8 in the forward direction is limited by the upper edge 64a of the cam bushing 60 (visible in FIG. 8). As also seen in FIG. 8, the front edge 64b formed in the cam bushing 60 limits the freedom of motion of the lancet holder 8 in the rear direction during the loading procedure.

Taken together, the edges 63a, 63b, 64a and 64b of the recesses 61 and 62 fashioned in the inner wall of the lancet drive rotor 13 thereby constitute a cam guide through which the two guide pins 31 travel. This preferred embodiment facilitates an extremely slim construction.

In the blood withdrawal device shown, both the helical slide surface 22 and the cam guide 30 are fashioned on a single rigid component (comprising two parts, namely the loading sleeve 59 and the cam bushing 60, for manufacturing reasons only). Such a rigid construction for the drive rotor 13 is preferred. Other configurations are, in principle, possible with which the required rotational coupling between the cam guide 30 and the helical path slide surface 22 is effected indirectly e.g. via a connection rod. Within the meaning of the invention, the drive rotor is always understood to be the unit which rotates about the main axis, independent of whether it consists of one or a plurality of components.

As shown, the loading cam 20 is preferentially fashioned as an integral part of the loading button 17. However, this is not absolutely necessary. Other designs are possible with which the loading cam 20 and the trigger button 27 are separate components. They must, however, be connected to each other in such a fashion that, when the loading button 17 is operated, the loading cam 20 moves synchronously with the loading button 17 along the linear loading path 23.

The blood withdrawal apparatus in accordance with the invention can have a very slender shape. Preferably the blood withdrawal device should have a maximum diameter of less than 20 mm. Use of a design in accordance with the invention even allows values of less than 15 mm.

Such a slender shape is important for easy carrying of the blood withdrawal device. More importantly, it advantageously allows a very low rotational moment of inertia for the lancet drive rotor. This low rotational moment of inertia permits loading of the lancet drive with a loading force of only approximately 11 Newton through a loading path of 15 mm using a relatively weak drive spring having a spring constant between approximately 25 to 35 Nmm. Despite ease of operation, the device provides extremely rapid and precise movement for the lancet with low vibration and associated minimal pain.

What is claimed is:

1. Blood lancet device for withdrawing blood for diagnostic purposes comprising
an elongated housing, the front end of which having an exit opening for the tip of a lancet,
a lancet holder for holding the lancet, the lancet holder being movable in the housing in the direction of its main axis along a predetermined puncturing path,
a lancet guide for guiding the lancet holder along the predetermined puncturing path and
a lancet drive having an elastic drive spring which can be locked by a locking device in the loaded state of the drive spring, the lancet drive converting after triggering of the locking device the tension release movement of the drive spring into a puncturing motion to move the lancet, held in the lancet holder, at high speed along the predetermined puncturing path in the puncturing direction until its tip emerges from the exit opening to produce a wound in a body part adjacent the exit opening, wherein
a double sided rotay/translatory transmission is provided in the housing,
a) the input side of the rotary/translatory transmission converting the motion of a loading button, which projects out of the housing at its rear end and moves along a linear loading path, into a rotational motion of a lancet drive rotor, the lancet drive rotor being rotated about a rotational axis running parallel to the axis of the device to load the lancet drive rotor by tensioning the drive spring and
b) the output side of the rotary/translatory transmission converting after triggering of the lancet drive a rotational motion of the lancet drive rotor driven by the drive spring into the puncturing motion in the direction of the main axis.

2. Blood lancet device according to claim 1, wherein the input side of the two-sided rotary/translatory transmission comprises a helical path provided on the lancet drive rotor and a loading cam connected to the loading button for motion therewith along the loading path and sliding via a loading cam contact surface along a slide surface of the helical path.

3. Blood lancet apparatus according to claim 2, wherein the slope ($\alpha$) of the helical path increases, at least in sections of its length in the direction towards the front end of the housing.

4. Blood lancet device according to claim 3, wherein the slope ($\alpha$) varies in such a fashion that the loading force required for moving the loading button during loading of the lancet drive is substantially constant, at least in sections of the loading path.

5. Blood lancet device according to claim 2, wherein the contact surface of the loading cam is slanted for area contact with the slide surface of the helical path along at least a portion of that half of the length of the helical path which is closer to the front end of the housing.

6. Blood lancet device according to claim 5, wherein a ramped starting section is provided on the end of the helical path which is closer to the rear end of the housing, the starting section having a slope corresponding to the slope of the contact surface.

7. Blood lancet device according to claim 2, wherein the helical path is formed on a loading sleeve constituting a portion of the lancet drive rotor, wherein the front end of the loading sleeve facing the exit opening surrounds the lancet holder.

8. Blood lancet device according to claim 2, wherein the lancet drive rotor comprises two parallel helical paths and two loading cams are connected to the loading button for movement with the loading button through the loading path, each of the loading cams sliding during loading of the lancet drive along a slide surface of one of the helical paths.

9. Blood lancet device according to claim 2, wherein the material forming the slide surface of the helical path comprises a polyacetal, preferentially a polyoxymethylene (POM).

10. Blood lancet device according to claim 2, wherein the material forming the contact surface of the loading cam comprises a styrene-acrylnitril-copolymer (SAN).

11. Blood lancet device according to claim 1, wherein the output side of the two-sided rotary/translatory transmission comprises a cam drive mechanism the cam drive mechanism comprising a recess in the lancet drive rotor defining a cam guide, and a control pin engaging into the recess and connected to the lancet holder, wherein at least a portion of the puncturing motion is defined by the rotational motion of the cam guide relative to the control pin during the rotational motion of the lancet drive rotor, during which the guide pin travels along the recess defining the cam guide.

12. Blood lancet device according to claim 11, wherein the return motion of the lancet holder is also defined by the rotational motion of the cam guide relative to the guide pin.

13. Blood lancet device according to claim 11, wherein two guide pins are connected to the lancet holder and engage into two differing recesses in the lancet drive rotor, wherein, during each phase of the rotational motion of the lancet drive rotor, one of the recesses guides one guide pin in rearward direction and the other recess guides the other guide pin in forward direction.

14. A kit for withdrawing blood for diagnostic applications, wherein the kit comprises a blood lancet device according to claim 1 and at least one lancet adapted to be held in the lancet holder thereof.

* * * * *